United States Patent [19]
Sorensen, III et al.

[11] 3,983,374
[45] Sept. 28, 1976

[54] DIGITAL SYSTEM FOR SLOPE AND CURVATURE CONTROL

[75] Inventors: Andrew J. Sorensen, III, Granada Hills; John A. Robinson, Chatsworth, both of Calif.

[73] Assignee: Uresco, Inc., Downey, Calif.

[22] Filed: June 20, 1975

[21] Appl. No.: 588,663

[52] U.S. Cl. ............................ 235/151.3; 73/67.8 S; 33/1 P
[51] Int. Cl.² ................. G01N 29/04; G06F 15/20
[58] Field of Search .................... 235/151.3, 151.1; 33/1 P; 73/DIG. 4, 104, 69, 67.8 S; 340/3 R; 356/240, 237

[56] References Cited
UNITED STATES PATENTS

| | | | |
|---|---|---|---|
| 3,134,099 | 5/1964 | Woo | 33/1 P |
| 3,309,913 | 3/1967 | Weighart | 73/67.8 S |
| 3,678,736 | 7/1972 | May | 73/67.8 S |
| 3,721,118 | 3/1973 | Jeffras | 73/67.8 S |
| 3,765,229 | 10/1973 | Spencer et al. | 73/67.8 S |
| 3,857,052 | 12/1974 | Beller | 73/67.8 S X |
| 3,863,496 | 2/1975 | Hiramatsu et al. | 73/67.8 S |

*Primary Examiner*—Edward J. Wise
*Attorney, Agent, or Firm*—John T. Matlago

[57] ABSTRACT

A digital control system is provided for controlling the indexing of the focussed beam of an ultrasonic transducer over a sloped or curved surface of a workpiece being inspected for flaws. To index the transducer to follow a sloped surface on the workpiece the angle of the sloped surface in half degree incrementation is setup and used to read out the sine and cosine functions from a memory. At the index time of a scan each of these functions is used to pass a portion of a preset number of clock pulses to provide vertical and horizontal clock pulses which respectively increment stepping motors to reposition the transducer along the sloped surface. To index the transducer to follow a curved surface on the workpiece, the radius of the circumferential path along which the transducer is to be moved is setup and used to help define when the transducer has moved along a chord of a half degree angle. At that time the angle setup defining the slope of the chord is incremented by one half degree, the transducer is gimballed by one half degree, and the sine and cosine functions of the incremented angle are read out of the memory and used to pass portions of the clock pulses provided at the index time of the next scan to thereby provide vertical and horizontal clock pulses which respectively increment stepping motors to move the transducer along a succeeding chord of a half degree angle along the circumferential path.

20 Claims, 15 Drawing Figures

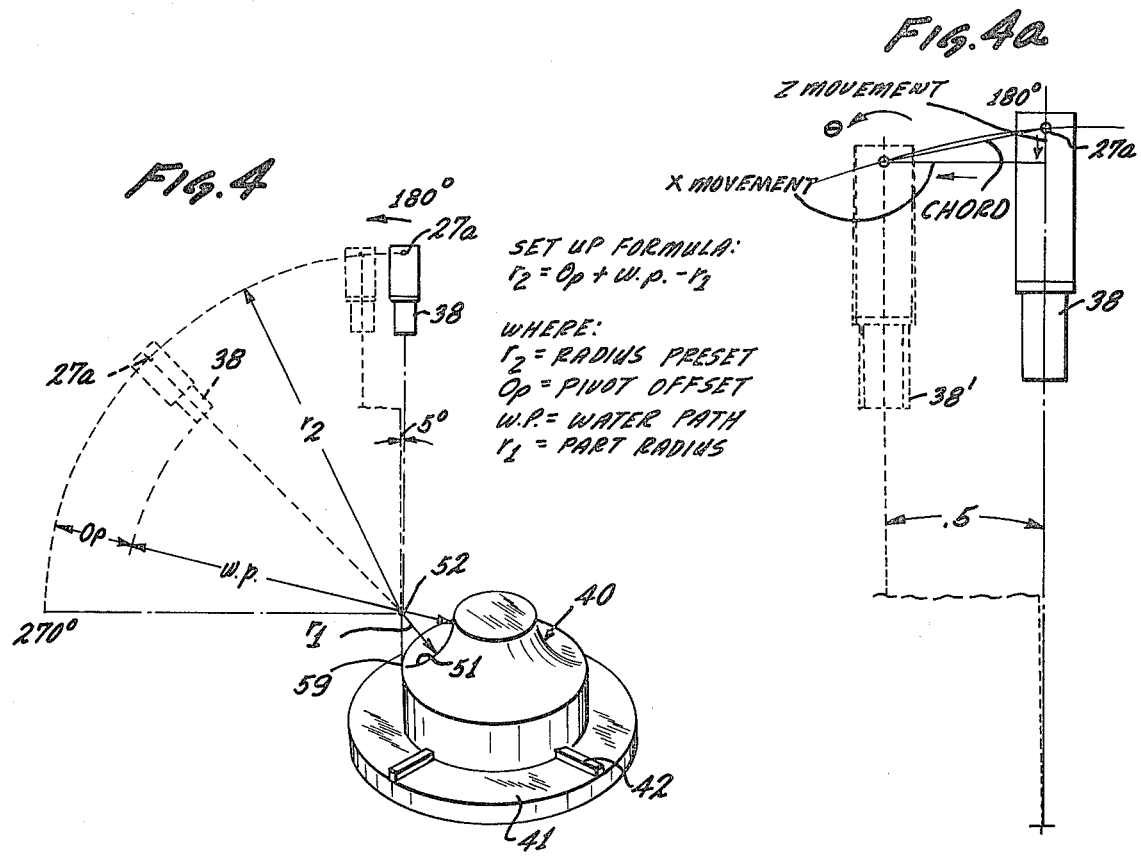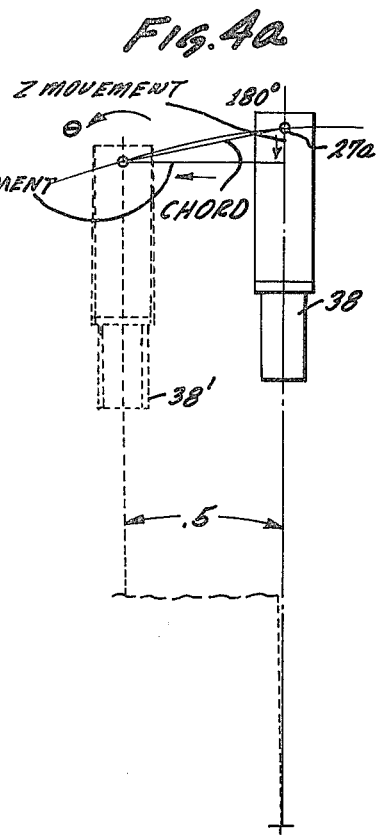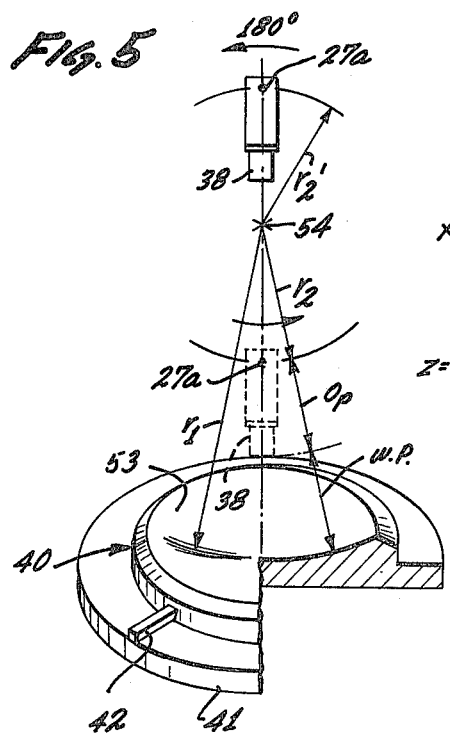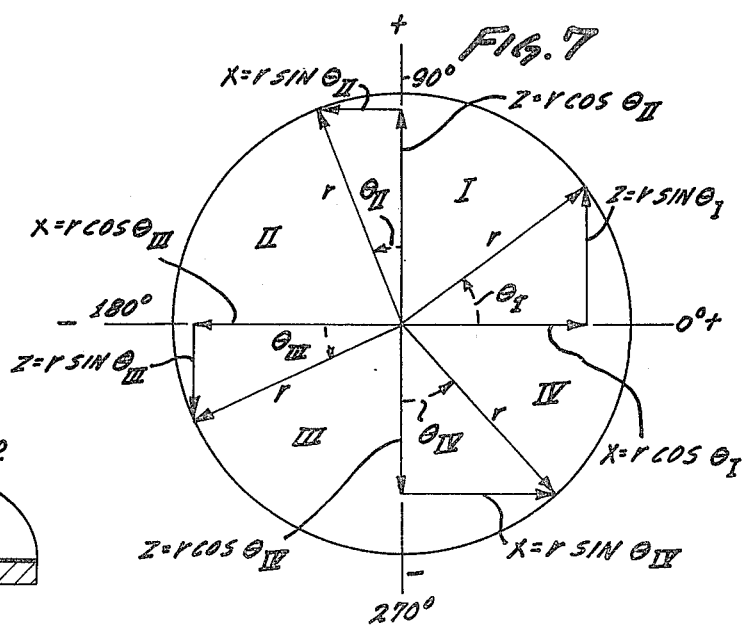

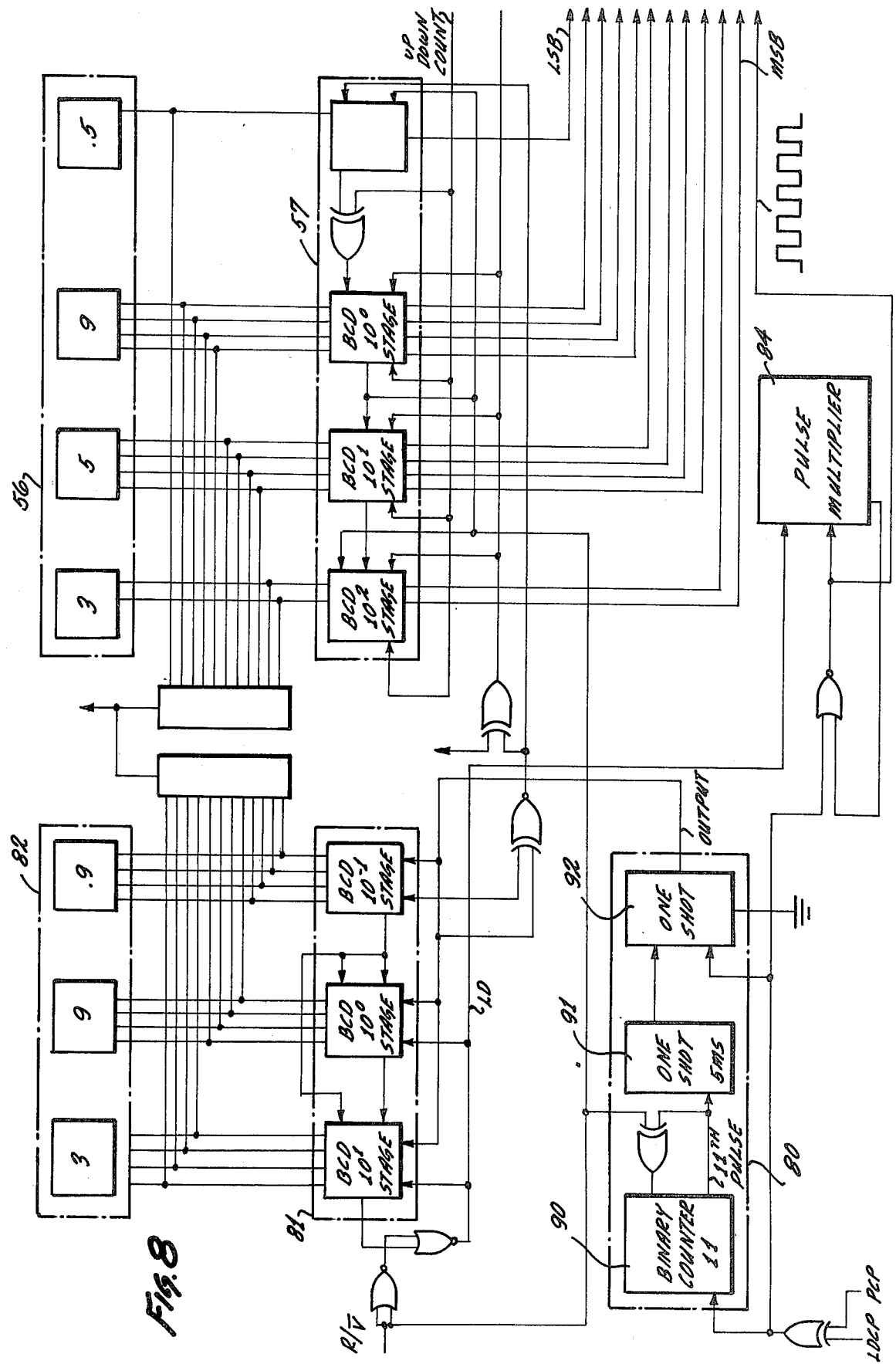

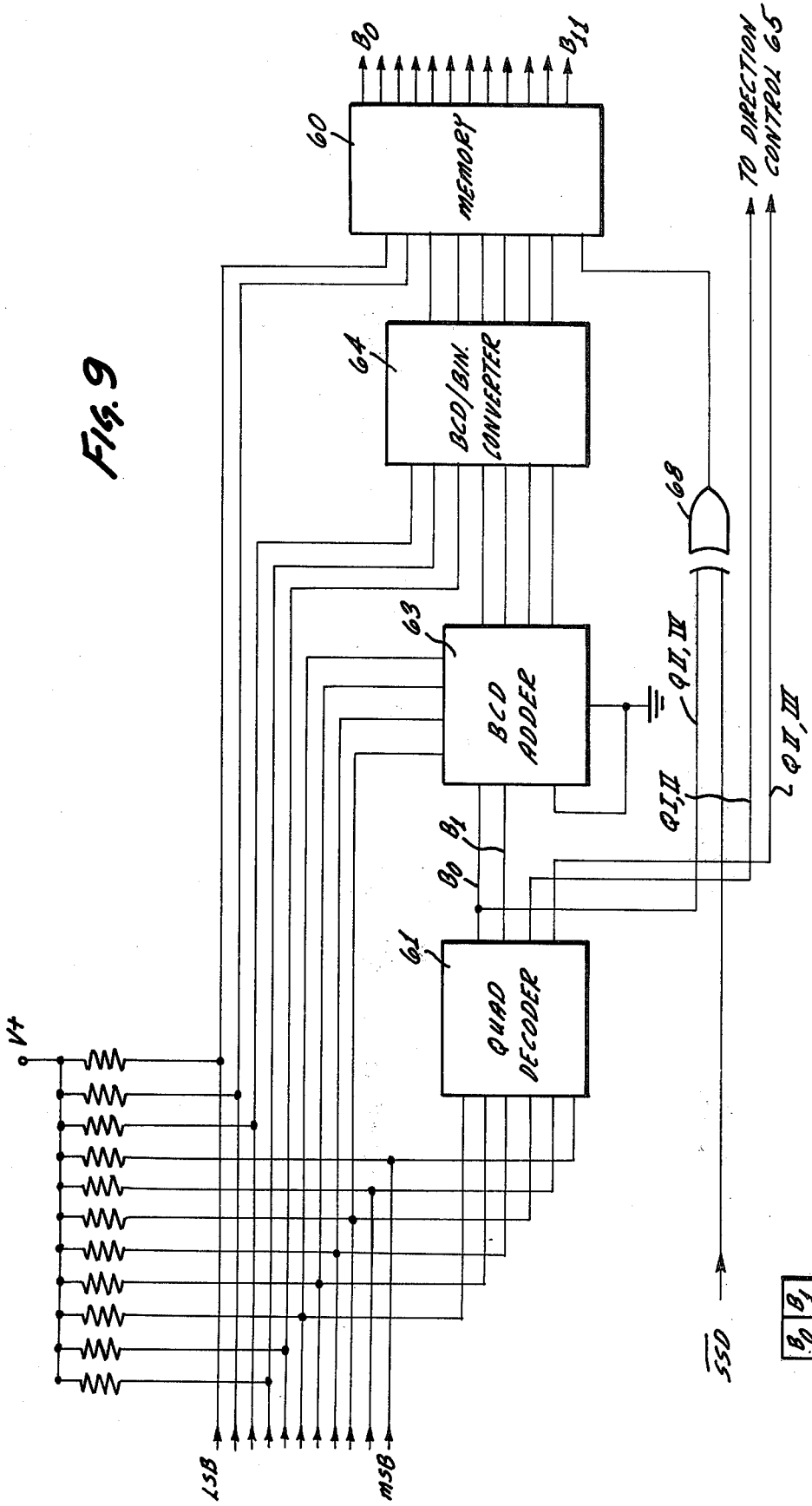

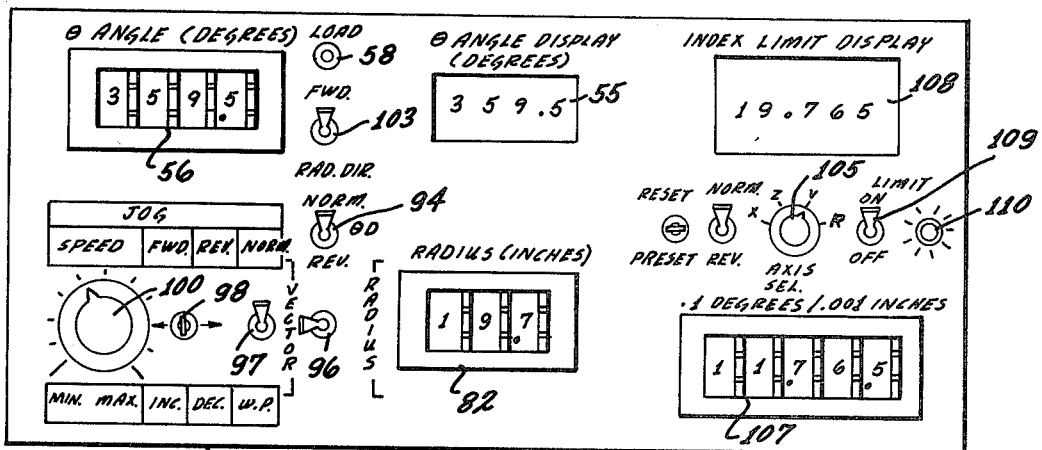
Fig. 11
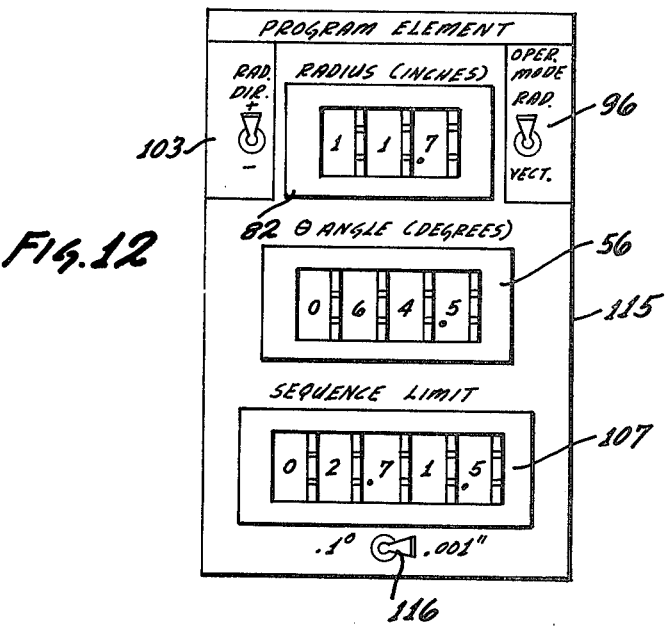
Fig. 12
Fig. 13
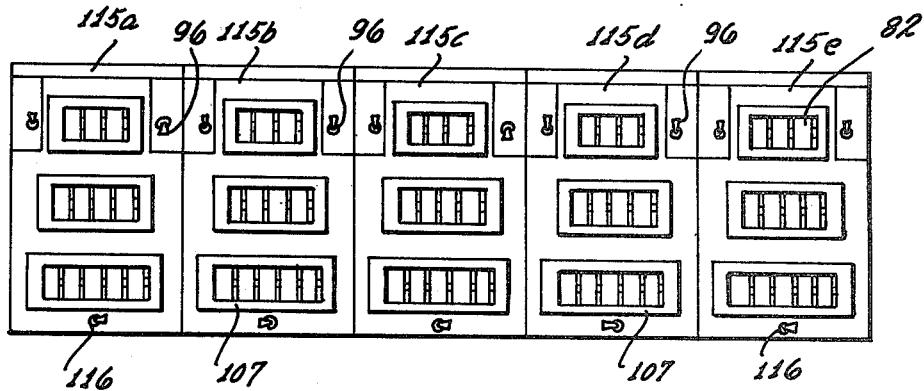

DIGITAL SYSTEM FOR SLOPE AND CURVATURE CONTROL

This invention relates to digital control systems for indexing an operating unit to track a sloped or curved surface and more particularly to such a system for indexing a ultrasonic transducer for use in nondestructive testing of the material of workpieces for flaws.

It is well known to inspect a workpiece for cracks or other imperfections by employing an ultrasonic transducer such as a piezoelectric crystal to scan the workpiece. The piezoelectric crystal when energized by an electrical stimulus radiates a beam of ultrasonic energy into the workpiece. The ultrasonic energy is then reflected back from a defect within the workpiece to the crystal whereby the mechanical vibrations thereof are translated back to electrical signals. By use of this method the time of arrival of the return signal indicates the presence and exact location of the defect within the workpiece.

In order to inspect cylindrical, frusto-conical, or portions of convex or concave curved surfaces on workpieces, the workpieces are mounted to rotate on a turntable in a tank of water along with the transducer so that a good ultrasonic coupling is possible. A bridge is mounted to move longitudinally on the tank by an X stepping motor and a carriage on the lower end of a tubular housing carried by the bridge is adapted to be moved vertically relative to the tank by a Z stepping motor. A manipulator is mounted on a gimbal axis on the carriage for movement by a gimbal stepping motor. The transducer is mounted on the manipulator with its longitudinal axis aligned therewith. In order to position the transducer by use of the slope control of the digital system so that its beam will be maintained normal to the sloped surface of the workpiece being inspected, the transducer is moved during the index time of a scan along a preset angle relative to the rotating workpiece by the X stepping motor and the Z stepping motor. In order to position the transducer by use of the curvature control of the digital system, so that its beam will be maintained normal to the circumferential surface of the workpiece being inspected, the transducer is not only indexed to be moved along chords of the circumferential path by the X and Z stepping motors but is also incrementally rotated at the end of each chord about its gimbal axis by the gimbal stepping motor.

In the past, complicated tape program reading systems and digital and/or analog computers have been needed to control the movement of the transducer by the stepping motors to provide the inspection of such sloped and curved surfaces. The system in accordance with the present invention eliminates the need for such numerical tape control and the extensive and elaborate use of digital and/or analog computer systems. Thus, the digital control system of the present invention is simply set up for the slope control by entering on the control panel an angle corresponding to the slope of the surface to be tracked. Moreover, the digital control system is simply set up for curvature control by simply entering on the control panel an angle corresponding to the slope of a fixed angular increment chord at the starting point of the circumferential surface to be tracked, and a radius corresponding to the circumferential path to be followed by the transducer.

In particular, many workpieces have very small radius concave surfaces which should be tested for cracks or other flaws. This presents a problem since the face of the transducer not only has an operational offset from its gimbal axis, but, in order to focus the beam of the transducer, it is necessary to position its face a distance equal to the focal length of the beam away from the surface being scanned. Thus, it is physically impossible to position the gimbal axis of the transducer at the center of the concave circumferential surface to be scanned. It is, therefore, evident that there is a need for control apparatus and a mode of operation thereof which can simply provide for inspecting small radius concave surfaces of workpieces by use of ultrasonic transducers.

Briefly, the digital control system of the present invention provides for controlling the indexing of an ultrasonic transducer such that its beam is focussed to track along a sloped or curved surface of a rotating workpiece. The system includes a memory which provides for digitally storing sine functions of angles corresponding to the slope of the surfaces to be tracked. To perform slope control by use of the digital control system an indication is provided of the angle of the sloped surface to be followed by the transducer. This angle is then used to address the memory to load its sine and cosine functions into sine and cosine registers. At the index time of a scan of the workpiece by the beam of the transducer, a preset number of index clock pulses provided by an index control simultaneously pass through a sine binary rate multiplier and a cosine binary rate multiplier in accordance with the functions loaded in the respective sine register and cosine register to provide separate trains of clock pulses. These respective trains of clock pulses are simultaneously applied to vertical and horizontal axis stepping motor means to index the transducer along its sloped path. To perform curvature control, in addition to providing an indication of an angle, which in this case is the starting angle, an indication is provided of the radius of the circumferential path to be followed by the transducer. At the index time of a scan a chord measuring circuit is provided for defining when the transducer has been moved by the index clock pulses a distance of a chord of a fixed angular increment at the radius indicated. The output of the chord measuring circuit is used to increase the angle by the fixed angular increment, to gimbal the transducer about its gimbal axis by the fixed angular increment, and to initiate the strobing of the memory with the new angle to obtain the new sine and cosine functions to be used at the index time of the next scan to control the movement of the transducer along the succeeding chord.

Accordingly, one of the objects of the present invention is to provide a digital control system which provides for indexing an ultrasonic transducer along a path parallel to a sloped surface of a workpiece.

Another object of the present invention is to provide a digital control system which provides for incrementally indexing an ultrasonic transducer along successive chords of a circumferential path and gimballing the transducer at the end of each chord such that its longitudinal axis is maintained at all times aligned with a radius of the curved surface being scanned by the beam of the transducer.

Another object of the present invention is to provide a digital control system which can be selectively made effective to control the movement of a transducer along a path which is parallel to either a sloped or curved surface of the workpiece.

Another object of the present invention is to adapt a programmable read only memory to provide the sine and cosine functions of angles ranging from 0° to 360° by storing therein only the sine functions of the angles ranging from 0° to 90°.

Another object of the present invention is to provide a circuit which enables the same source of clock pulses being used to provide the linear increment of movement of a transducer to be adjusted for use in determining when the transducer has been repositioned along the chord of a predetermined angular increment at any preset radius such that the transducer can be gimballed about its gimbal axis to maintain it aligned with a radius of the surface of the workpiece being scanned.

Another object of the present invention is to provide a novel virtual scan movement of a transducer such that the beam of the transducer can be controlled to scan small radius concave surfaces.

Yet another object of the present invention is to provide a digital control system which can be automatically operated by successive preset program elements to perform a series of different scanning functions on a workpiece mounted for rotating on a turntable.

Yet another object of the present invention is to provide a digital control system which can be set up to continue to advance a transducer along a sloped or circumferential path until a limit reading is obtained.

With these and other objects in view, the invention consists in the construction, arrangement and combination of the various parts of the system whereby the objects contemplated are attained, as hereinafter set forth, pointed out in the appended claims and illustrated in the accompanying drawings:

In the drawings:

FIG. 4 illustrates a workpiece having a concave circumferential surface with a small radius which can be inspected by controlling the transducer with the use of the digital control system of the present invention;

FIG. 4a is an enlarged diagram illustrating the action produced by the stepping motors on the transducer by the digital control system of the present invention when operating in the curvature control mode;

FIG. 5 illustrates a workpiece having a concave surface with a large radius that can be inspected by controlling the transducer with the use of the digital control system of the present invention;

FIG. 7 is a diagram for use in identifying the quadrants of a circle and explaining the strobing of the sine and cosine functions from the memory and the determination of the sign of these functions;

FIG. 8 is a block diagram illustrating in greater detail the circuits provided for receiving and manipulating the data setup by the thumbwheel switches on the control panel;

FIG. 9 is a block diagram illustrating in greater detail the circuits provided for modifying the input angle used to address the memory and for determining the signs of the functions read out of the memory;

FIG. 9a is a table showing the states of the output of the quad decoder indicative of the quadrants of the input angles;

FIG. 11 illustrates a control panel used in conjunction with the system of the present invention;

FIG. 12 illustrates a program element which may be used with the system of the present invention; and FIG. 13 illustrates a plurality of program elements which operate in sequence to automatically control the different functions performed by the digital control system of the present invention.

Figure 1:
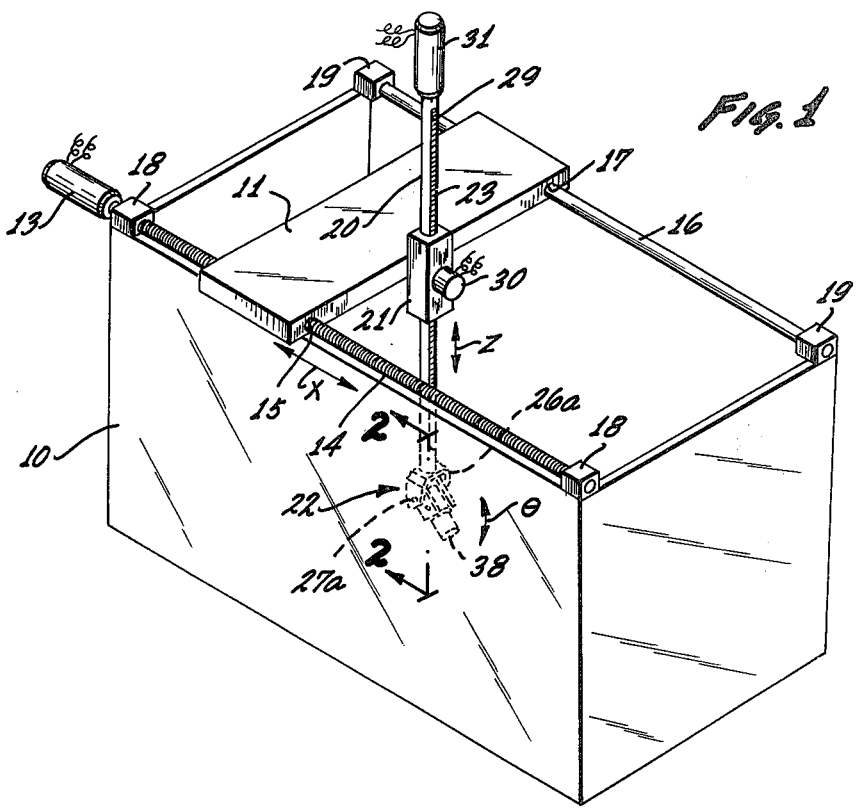
FIG. 1 illustrates a bridge and carriage mounting for an ultrasonic transducer in a water tank which is used to perform nondestructive testing of workpieces.
Figure 2:
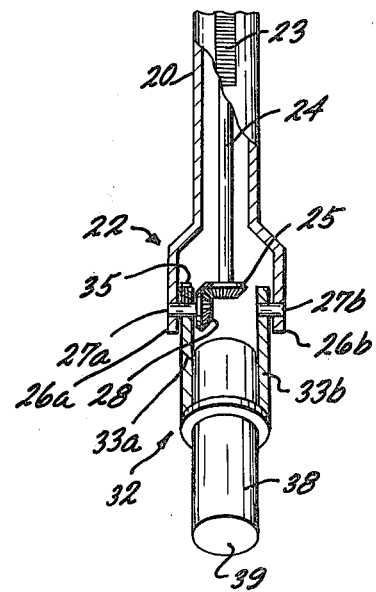
FIG. 2 is a sectional view of the carriage as taken in the direction of arrows 2—2 in FIG. 1.

Referring to the drawings, FIG. 1 shows a tank 10 provided with a bridge 11 which spans across the top thereof. The bridge 11 has a longitudinal lead screw 14 engaged in a threaded bore 15 provided along the front side thereof and a longitudinal guide rod 16 having a sliding fit in a bore 17 provided along the rear side thereof. The lead screw 14 has its ends mounted in bearing supports 18 provided on the top front corners of the tank. The guide rod 16 has its ends fixed on supports 19 provided on the top rear corners of the tank. An X stepping motor 13 is mounted on one of the bearing supports 18 and connected to rotate the lead screw 14. A vertically disposed tubular housing 20 extends through an opening on a bracket 21 attached to the front end of the bridge 11. The housing 20 is provided on the lower end thereof with a carriage 22 having spaced flat sides 26a and 26b. The carriage is submerged in a liquid couplant, such as water, filling the tank 10. A rack 23 is mounted in the housing 20 adjacent to an elongated opening 29 extending along the front of the housing. A Z stepping motor 30 mounted on bracket 21 has its drive shaft connected to a pinion (not shown) which engages rack 23. As shown in FIG. 2, shaft 24 extending down through the center of the housing 20 has a bevel gear 25 attached on the lower end thereof. A gimbal stepping motor 31 mounted on the upper end of housing 20 is connected to rotate shaft 24. A pair of transverse stub shafts 27a and 27b are respectively pivotally mounted on the flat sides 26a and 26b of carriage 22. The inner ends of stub shafts 27a and 27b pass through openings in the flat sides 33a and 33b of a U-shaped manipulator 32. Bolts 35 fix the sides of the manipulator to the shafts 27a and 27b. One of the stub shafts 27a is provided with a bevel gear 28 on the inner end thereof which meshes with the bevel gear 25 on the lower end of the shaft 24. An ultrasonic transducer 38 has its upper end fixed in position in an opening on the bottom of the manipulator 32.

As is now clearly illustrated in FIG. 1, the transducer 38 fixed on the end of the manipulator 32 can be moved horizontally in either direction by incrementally energizing the X stepping motor 13 to rotate the lead screw 14. The transducer 38 can be moved vertically in either direction by incrementally energizing the Z stepping motor 30 which drives the pinion engaging the rack 23. Furthermore, the transducer 38 can be gimballed in either direction about the axis of stub shafts 27a and 27b so that its longitudinal axis is normal to a surface having an angle $\theta$ with respect to the horizontal by incrementally energizing the gimbal stepping motor 31. The pivoting of the transducer about the axis of the stub shafts 27a and 27b will herein after be referred to as the gimbal point 27a of the transducer 38.

Figure 3:
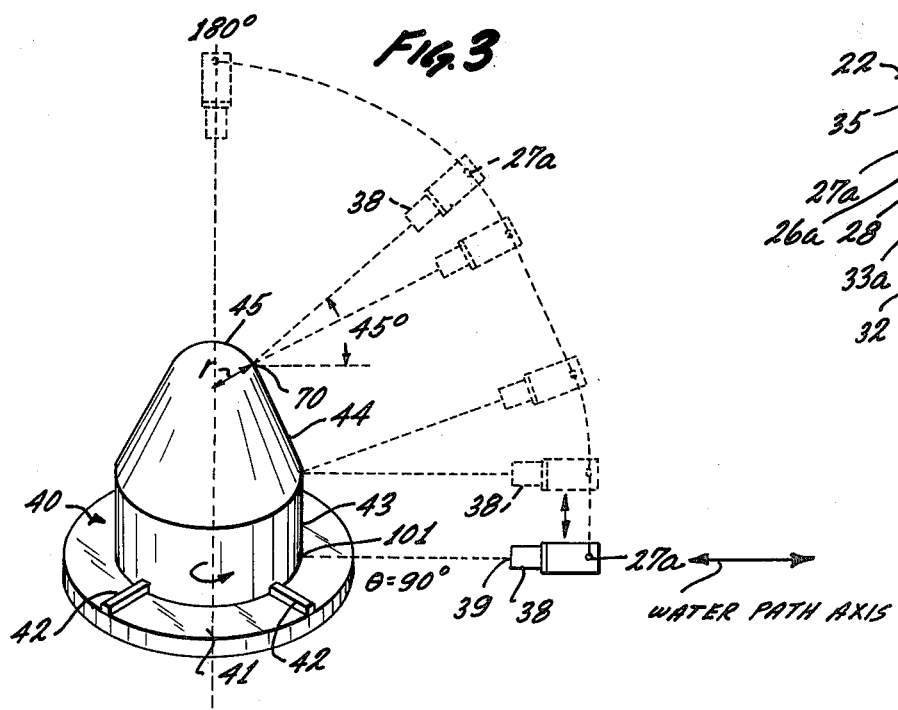
FIG. 3 illustrates a typical workpiece which can be inspected by controlling the transducer with the use of the digital control system of the present invention.

Typically rotating workpieces 40 which can be effectively scanned by the transducer 38 under control of the digital control system of the present invention are shown in FIGS. 3, 4 and 5. The workpieces 40 are concentrically held on a rotating turntable 41 by three jaws 42. Initially to be pointed out is that the transducer 38 used for ultrasonic testing, and especially the type used for high resolution testing, is much like an optical device in that the beam it emits must be focused on or beneath the surface of the workpiece being scanned. For example, if the transducer 38 has a focal length of 5 inches, its face 39 should be spaced from the surface of the workpiece 40 to be inspected such that the focal point of the beam is just inside the surface or maybe just outside it. Thus the focal length of a transducer 38 is referred to as the water path at a particular frequency.

Referring to FIG. 3, a workpiece 40 in the form of a nose cone is shown mounted on the rotating turntable 41. The workpiece includes a lower portion having an upright cylindrical surface 43, an intermediate portion having a frusto-conical surface 44, and an upper portion having a spherical surface 45. The transducer 38 is initially located opposite the lower end of the upright cylindrical surface 43 with its face 39 spaced therefrom a distance equal to its focal length. The digital control system of the present invention is then set to cause the gimbal point 27a of the transducer 38 to be indexed along a path parallel to the vertical surface 43 each index time of the scan. This is accomplished by manually placing the angle $\theta$ equal to 90° in the angle thumbwheel switches 56 of the digital control system panel 49. Thus as the workpiece 40 in FIG. 3 rotates, the beam of the transducer 38 scans successive paths along the surface 43 of the rotating workpiece. At the end of each rotation of the turntable 41, the digital control system of the present invention causes the transducer 38 to be indexed a fixed increment spaced upwardly and parallel to the vertical surface 43 such that its beam scans along a new path of the surface 43. After the transducer 38 has been indexed to the upper edge of the vertical surface 43, the digital control system of the present invention can then be manually reset by introducing the angle $\theta$ of the inclined surface 44 into the digital control system. This causes the transducer 38 to be indexed each index time of a scan along a path parallel to the inclined surface 44. Likewise, after the transducer 38 reaches the upper end of the inclined surface 44, the digital control system of the present invention can be reset and operated to cause the transducer 38 to be indexed along a circumferential path parallel to the spherical surface 45 on the upper end of the workpiece 40.

FIG. 4 illustrates a workpiece 40 which has a concave surface with a very small radius. This workpiece 40 is similarly mounted to rotate on a turntable 41. As will be subsequently described, the digital control system of the present invention enables the surface 51 having a small radius to be inspected by using a virtual scan set up for the transducer 38. In such a set up, the transducer 38 is displaced a distance from the surface 51 equal to several times its radius and caused to be rotated about the center of curvature 52 of the concave circumferential surface 51.

FIG. 5 illustrates a workpiece 40 having a circumferential surface 53 with a large radius, which is to be inspected for flaws by the ultrasonic transducer 38. With such a large radius surface 53 the transducer 38 can be positioned for movement along a circumferential path located either outside the center of curvature 54 or along a circumferential path located within the center of curvature 54 of the circumferential surface 53 to be inspected. The circumferential path selected for the transducer 38 depends on the focal length, W.P., and the pivot offset, $O_p$, of the transducer being used. In either position, the digital control system can be setup to cause the transducer 38 to be indexed along a circumferential path which causes the beam to scan the circumferential surface 53. As noted, in either position, the gimbal point 27a of the transducer is caused to move at a fixed distance $r_2$ (or $r_2'$ which is equal to $r_2$) about the center of curvature 54 of the circumferential surface 53 being scanned by the transducer.

The general overall block diagram of the digital control system shown in FIG. 6 will next be described. First to be discussed are the functional blocks and the mode of operation of the digital control system which is referred to as the slope or vector control. The slope control provides for indexing the transducer along a linear or sloped surface of the workpiece 40 being inspected. Thus the angle $\theta$ of the linear path, along which the transducer 38 is to be indexed to scan an inclined surface with its beam, is entered by setting angle thumbwheel switches 56 which set up an angle in BCD format into the angle counter 57. The transducer 38 is then initially positioned manually by controlling the gimbal stepping motor 31 from the control panel 49 such that its axis is aligned to be normal to the inclined surface of the workpiece. The transducer 38 is then positioned along its water path axis so as to be at the correct focal point and is positioned along its normal path of movement so as to be at the desired starting point.

Next to be described is the memory 60 of the digital control system which provides for storing in binary format the sine and cosine functions which are used to reposition the transducer 38 each time it is indexed during the index time of a scan. It should be understood that the memory 60 may be a conventional programmable read only memory programmed to function as herein described. Inasmuch as the X stepping motor 13 provides for only a longitudinal, i.e., a horizontal, linear movement of the transducer 38 relative to the workpiece 40, and the Z stepping motor 30 provides for only a vertical linear movement of the transducer 38 relative thereto, in order to move the transducer 38 along a path parallel to an inclined surface having an angle $\theta$ with the horizontal, a combination of simultaneous linear movements of the transducer by these two stepping motors is required. The distance along the path is the hypotenuse $h$ of a right angled triangle having a horizontal side defined by $h \cos \theta$ and a vertical side defined by $h \sin \theta$.

The scheme of the present invention is to divide the circumference of a circle into ½ degree increments. Thus the circumference is divided into 720 equal parts. Inasmuch as the absolute value of the sine of an angle is repetitious every 90°, the memory 60, which may be a programmable read only memory, is only provided with sine values of ½ degree increments between 0 to 90°. Thus the memory only stores sine values in ½ degree increments for the first quadrant. As will be explained subsequently, this information in the memory 60 is all that is needed to obtain the value of both the sine and cosine for all angles in ½° increments from 0° to 360°.

It should now be clear that for any input angle other than the first quadrant, a quad decoder 61 operates to modify the angle input to a BCD adder 63. The output of the BCD adder 63 is then converted to binary format in the BCD/BIN converter 64 and used to address the memory 60. As will be subsequently described, the quad decoder 61 further operates to provide information to a direction control circuit 65 which determines the direction of the sine and cosine functions read from the memory 60. The quad decoder 61 and the BCD/BIN converter 64 each may be a conventional read only memory arranged to operate as described.

When operating in the slope control mode, and having placed the angle in the angle thumbwheel switches 56, upon closing the manual load switch 58 on the control panel 49 (FIG. 11), a register control 66 provides a signal to first strobe the sine of the input angle from the memory 60 into a sine register 67. Following this read out, this register control 66 generates a sine strobe delay signal SSD which passes through an exclusive or gate 68 and causes the output of the BCD/BIN converter to be complemented such that this time that it addresses the memory 60, the sine of the complement of the input angle is read out. Since the sine of the complement of the input angle is the cosine of the input angle, this latter information is read out into a cosine register 69.

In connection with the reading of memory 60, it should be noted, as shown in FIG. 7, that in quadrants II and IV, the directions of the sine function and cosine function are reversed. Thus, as indicated in FIG. 9a, a binary bit $B_o$ provided by the quad decoder 61 is equal to 1 when the input angle is in the quadrants II and IV. Thus, this bit $B_o$ when true is used to complement the address such that the first function read out of the memory 60, although it is the cosine, is strobed into the sine register 67, and the second function read out of the memory 60, although it is the sine, is strobed into the cosine register 69. The outputs of the sine register 67 and cosine register 69 are then fed to a sine BRM 71 (Binary Rate Multiplier) and a cosine BRM 72, respectively. This completes the general description of the digital control system including the loading of the sine register 67 and the cosine register 69 to enable the system to thereafter operate in the slope control mode.

Now then during the index time of each scan of the workpiece 40 by the transducer 38, i.e., at the end of each turn of the turntable 41 on which the workpiece 40 is mounted, a switch 73 is closed on the index control 74 causing a number of pulses, the number being determined by presetting knob 76 on the index control 74, to be simultaneously fed into the sine BRM 71 and the cosine BRM 72. These binary rate multipliers 71 and 72 are standard components which serve to pass therethrough during each index time of a scan only a proportional number of the pulses supplied by index control 74, the number, i.e., the proportional number of pulses in each case, corresponding to the contents of the sine and cosine registers 67 and 69. Thus, for example, if each pulse corresponds to a value of .001 of an inch, and if 250 pulses are supplied by the index control 74 each index time of a scan, a portion of these 250 pulses corresponding to the value of the sine function in the sine register 67 will pass through the sine BRM 71, and portion of these 250 pulses corresponding to the value of the cosine function in the cosine register 69 will pass through the cosine BRM 72. These sine and cosine pulses are then fed into direction control 65 along with information from the quad decoder 61 as to the direction to be attached thereto, and the pulses are then fed to the translators 78 and 79 of the X and Z stepping motors 13 and 30, respectively. The sine BRM 71 and cosine BRM 72 may be standard commercial logic components manufactured by Texas Instruments, Inc., Dallas, Texas bearing Model No. 7497 TTL.

When operating in the slope control mode, it should now be clear that once the transducer 38 has been initially manually positioned to the desired angle $\theta$ and the sine and cosine register 67 and 69 have been loaded by closing load switch 58 on the control panel 49, the index control 74 thereafter is switched on each index time of a scan of the transducer to provide a fixed number of pulses which pass simultaneously through the sine BRM 71 and the cosine BRM 72. The train of pulses from these binary rate multipliers, after being given a direction as determined by the direction control 65, are then fed through translators 78 and 79 to increment the X and Z stepping motors 13 and 30, respectively.

Figure 6:
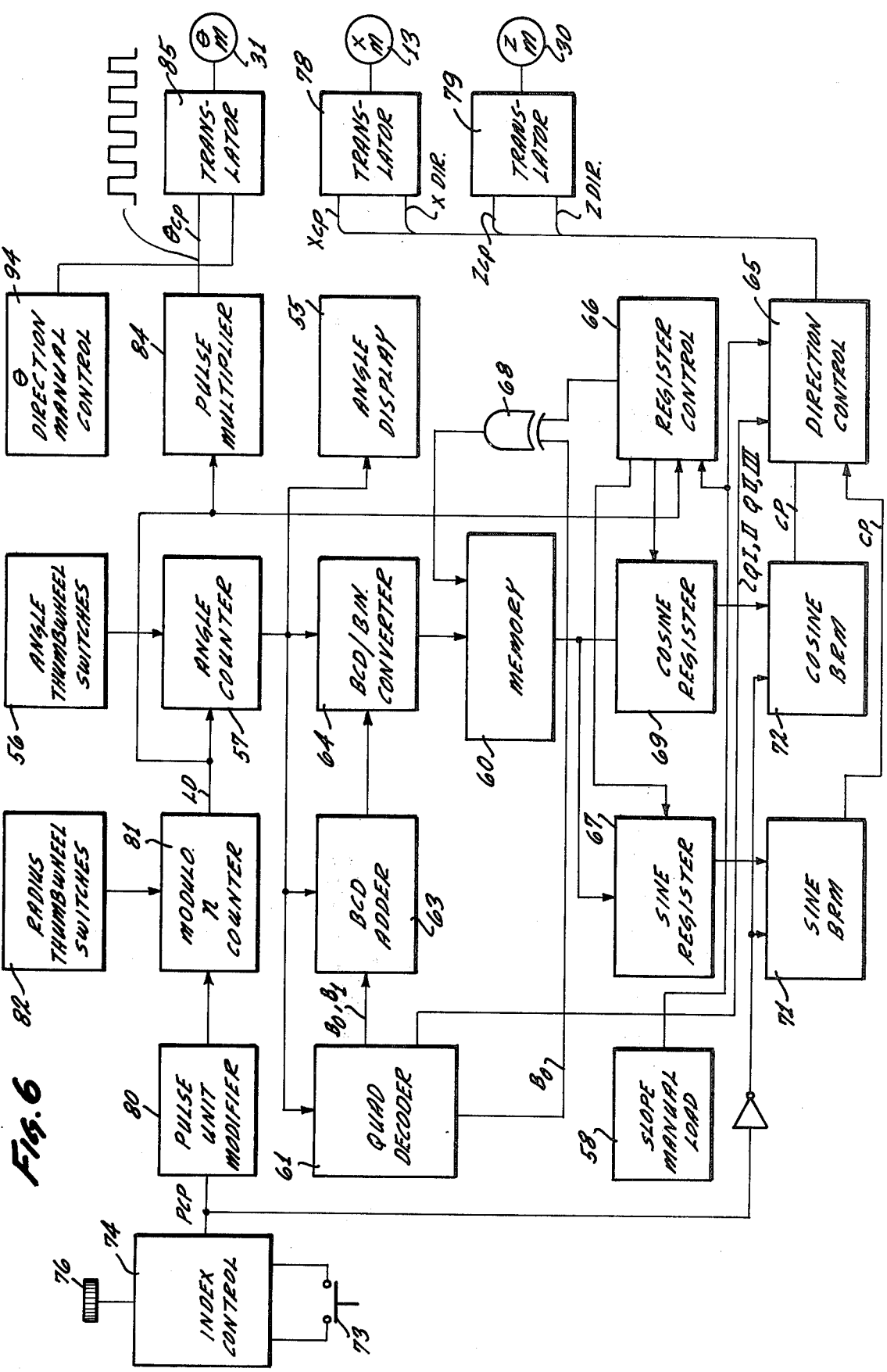
FIG. 6 is an overall block diagram of the digital control system for operating the stepping motors to control the transducer to perform an ultrasonic nondestructive inspecting of sloped or curved surfaces of a workpiece.

The functions of the block diagram of FIG. 6 so far described relate to the slope control mode of operation of the digital control system which provides for incrementally positioning a transducer 38 along a path parallel to but spaced from a sloped surface of the workpiece 40. However, as previously mentioned, the block diagram of FIG. 6 also includes the block functions needed for the curvature or radius control mode of operation of the digital control system which provides for positioning the transducer 38 incrementally along a circumferential path parallel to but spaced from a circumferential surface on a workpiece 40. The curvature control actually includes all the block functions of the slope control plus other block functions. Thus, as shown, in FIG. 6, the unit pulses, pcp, supplied by the index control 74, in addition to being fed to the sine BRM 71 and the cosine BRM 72 are also fed to a pulse unit modifier 80 which operates to modify the unit value of the pulses provided by the index control 74 for linear movement of the transducer by the pulses supplied by the sine and cosine BRM's 71 and 72. The purpose of this modification of the unit pulse is so that the pulses will be operable for use in defining the movement of the transducer along a chord of a ½° angle at a 1 inch radius which is being used as a standard of measurement. As will be subsequently described in greater detail, the modified unit pulses are further modified by a modulo $n$ counter 81 which is set up in accordance with the radius thumbwheel switches 82 on the control panel 49. Thus an output pulse 83 from the modulo $n$ counter 81 indicates that a number of modified unit pulses have been received corresponding to the length of a chord of a ½° angle located at the radius setup in the radius thumbwheel switches 82. The modulo $n$ counter 81 thus functions as a radius adjuster. The output pulse LD of the modulo $n$ counter 81 is used to advance the angle counter 57 by a ½° increment and is also fed to a pulse multiplier 84 which provided 5 pulses to translator 85 for each input pulse to increment the gimbal stepping motor 31 a ½° increment.

The pulse LD fed out of the modulo $n$ counter 81, in addition to being fed to the pulse multiplier 84 to gimbal the transducer, is also fed to the register control 66 which operates to initially access the memory 60 to load the sine function of the incremented angle in the angle counter 57 into the sine register 67, and then, after the SSD pulse is supplied, operates to again access the memory 60 to load the cosine function of the incremented angle in the angle counter 57 into the cosine register 69. This action is sufficiently fast such that it takes place between successive clock pulses provided by the index control 74. Note that the pulse rate output of the index control 74 varies between 1 to 200 pulses per second whereas the pulse action of the electronic circuits, such as the register control 66 and the memory 60, is on the order of microsecond operation. Thus during the index time of a scan, when in the curvature control mode of operation, the digital control system causes the transducer 38 to be incrementally moved along a chord of a ½° angle by the sine and cosine functions read out of the memory 60 to the extent that these readings control the since BRM 71 and the cosine BRM 72. Further, the gimbal stepping motor 31 is stepped to rotate the transducer 38 about its gimbal point 27a to maintain its beam normal to the surface being scanned. It should be now evident during the curvature control, as illustrated by FIG. 4a, that the digital control system operates to automatically initiate the gimballing as well as the sine and cosine movement of the transducer 38 along a circumferential path spaced from and parallel to the curved surface of the workpiece being inspected.

Figure 10:
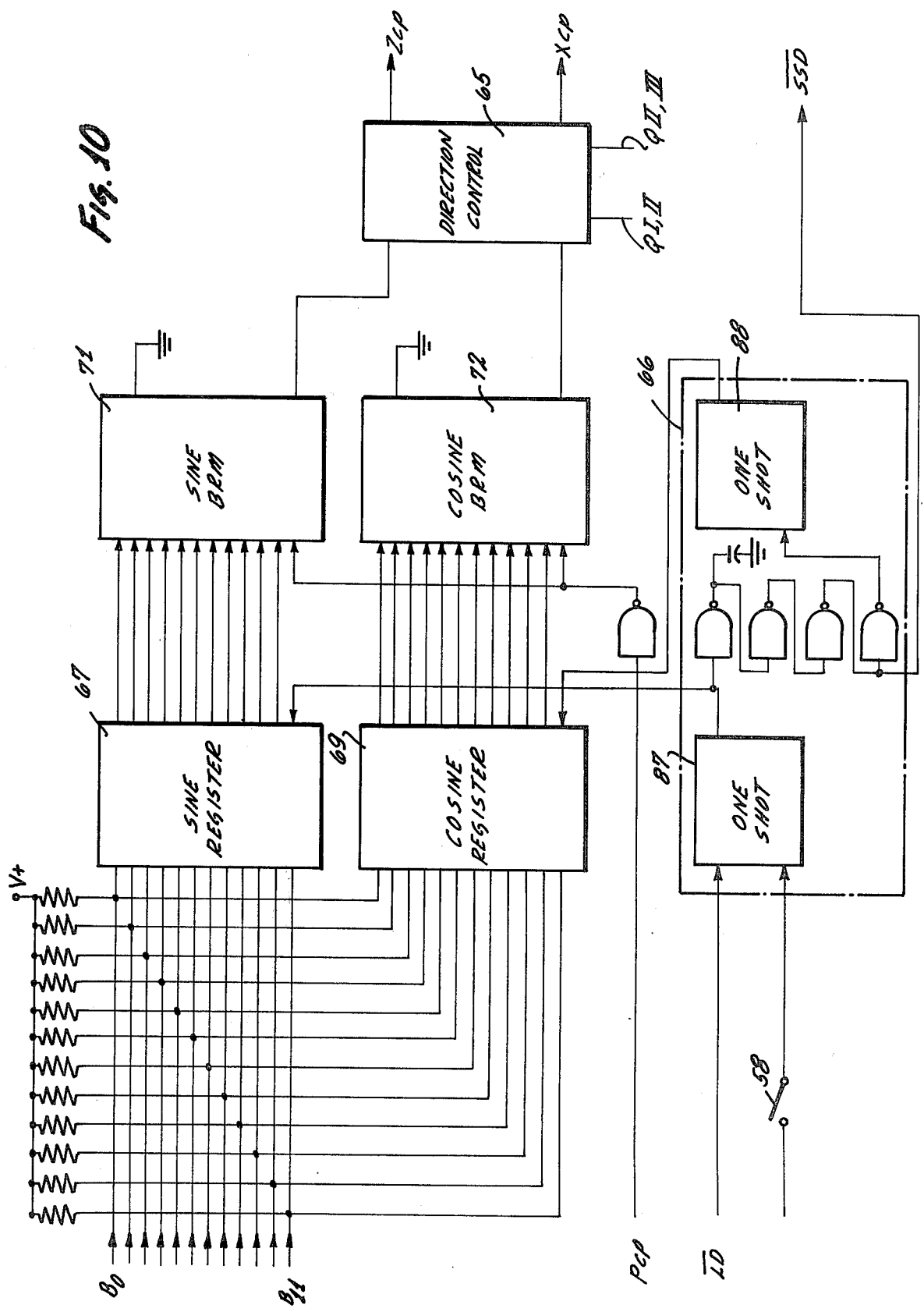
FIG. 10 is a block diagram illustrating in greater detail the circuits for utilizing the data read out of the memory to provide signals to control the X and Z stepping motors.

A more detailed description of the slope control will next be presented in connection with FIGS. 8, 9 and 10 which show more detailed showings of the block functions in FIG. 6.

Thus, as shown in FIG. 8, an angle from 0° to 360° in half degree increments as dialed in the thumbwheel switches 56 of the control panel 49 is transferred to be setup in BCD format in the stages of the angle counter 57. The single bit output of the lowest order half angle digit stage indicates either the absence or presence of a half angle. The units and tens order BCD stages are conventional. The hundreds order BCD stage is limited to provide two outputs since it never indicates beyond the digit three.

The outputs of the angle counter 57, in BCD format, as shown in FIG. 9, are fed to the quad decoder 61, the BCD adder 63 and the BCD/BIN converter 64. Since the output of the half angle stage is limited to either indicating 0° or 0.5° it is already binary and is fed directly to the memory 60 for addressing purposes. The first binary bit of the limits digit does not change in going from the binary to the BCD format and so it is also fed directly to the memory 60. The remaining three binary bits of the BCD format of the units digit are fed directly to the BCD/BIN converter 64.

The four binary bits of the tens order BCD digit are fed directly to the BCD adder 63 and also fed directly to the quad decoder 61. In addition, the last two binary bits of the hundreds order BCD digit are fed out to the quad decoder 61. From the data fed into the quad decoder 61, a determination is made as to which quadrant the input angle is in, and, if necessary, modifies the tens order BCD digit of the input angle. For the first 90 degrees, that is, the first quadrant, nothing has to be done to alter the input angle. Thus for the first 90° the input angle, after being converted to binary format, is effectively presented to the memory 60 as an address for first outputting the sine and then the cosine upon request from the register control 66. If the input angle is greater than 90 degrees it is necessary to reconstruct the input angle. For example, if the input angle is 120 degrees, the quad decoder 61 senses the input angle is in the second quadrant and introduces 10 into the BCD adder 63 to add to the input angle, at the same time dropping the highest order BCD digit, to thus provide the corrected BCD angle $\theta_{II}$ of 30 degrees. This BCD angle is fed into the BCD/BIN converter 64 to provide, along with data from the quad decoder 61 indicating the quadrant of the input angle, a binary address corresponding to 30 degrees. Upon a request from the register control 66 this address, which is actually complemented in this quadrant as hereafter described, is used to read the memory 60 to provide on its output a twelve bit binary number in parallel which is the sine function of the address. Upon a further request from the register control 66 the address is again complemented to read the memory 60 to provide on its output a twelve bit binary number in parallel which is the cosine function of the address.

It should now be evident that if the input angle is in the first quadrant, the quad decoder 61 has no effect on the input angle. If the input angle is in the second quadrant, the quad decoder 61 operates to add 10 to the tens order digit in the BCD adder 63 and discards the overflow to obtain the corrected input angle. If the input angle is in the third quadrant, the quad decoder 61 operates to add 20 to the tens order digit in the BCD adder 63 and discard the overflow to obtain the corrected input angle. In a similar manner, if the input angle is in the fourth quadrant, the quad decoder 61 operates to add 30 to the tens order digit in the BCD adder 63 and to discard the overflow to obtain the corrected input angle. The quad decoder 61 may be a programmable read only memory available from Intersil, Inc. of Cupertino, California, which has been programmed to operate in the manner described.

It should be noted, by reference to FIG. 7, that when the input angle is in quadrants I and III the sines are vertically disposed and the cosines are horizontally disposed. However, when the input angle is in quadrants II and IV the sines of the angles are horizontally disposed and the cosines are vertically disposed. Accordingly, as indicated in FIG. 9a, the $B_o$ output of the quad decoder 61 when 0 indicates that the angle is in quadrants I and III and when 1 indicates the angle is in quadrants II and IV. Thus, when in the latter, the input address to the memory 60 is complemented to get the other function out first.

As previously described, in response to a manual load switch 58 on the control panel 49, the register control 66 is initiated to request first the sine of the input angle addressing the memory 60. Thus a signal from load switch 58 triggers a one shot multivibrator 87 (FIG. 10) in register control 66 which after a delay is used to request the sine from the memory 60 and load it in the sine register 67. Then, after a second delay caused by a second one-shot multivibrator 88, the register control 66 is operated to request the cosine from the memory 60 and load it in the cosine register 69.

Thus the memory 60 is strobed first with the binary address of the input angle to load the sine function into the sine register 69 and then the memory 60 is strobed via the exclusive "or" gate 68 with the complement of the binary address of the input angle to load the cosine function into the cosine register 69. The 12 bit binary numbers in the sine register 67 and cosine register 69 are then fed to the sine BRM 71 and the cosine BRM 72. At each index time of a scan, thereafter, the switch 73 of the index control 74 is closed by the rotating turntable 41 and the sine BRM 71 and cosine BRM 74 have as an input the preset clock pulses, pcp, supplied by the index control 74. The outputs of the sine BRM 71 and cosine BRM 72 are thus a function of the binary number in the associated sine or cosine registers 67 and 69. The sine BRM 71 and cosine BRM 72 then both output their clock pulses to the direction control 65. The direction control also receives information from the quad decoder 61 which determines which quadrant the input angle is in and dictates the sign to be attached to the respective X and Z clock pulses.

Thus if the quad decoder 61 indicates that the input angle is in quadrants I and II, the information would be forwarded to the direction control 65 to assign a positive direction to the Z clock pulses being passed through the sine BRM 71. Otherwise the input angle would be in the III or IV quadrants and the Z clock pulses would be assigned a negative direction. Likewise, if the quad decoder 61 indicates that the input angle is in the II or III quadrants, the information would be forwarded to the direction control 65 to assign a negative direction to the X clock pulses being passed through the cosine BRM 57. Otherwise, the input angle would be in the I and IV quadrants and the X clock pulses would be assigned a positive direction. The direction control circuit 65 may be a standard commercial logic component of the type supplied by Texas Instruments, Inc., Dallas, Texas bearing Model No. MUX (74157). These Z and X clock pulses are then fed into translators 78 and 79 which energize the respective X stepping motor 13 and the Z stepping motor 30 to index the transducer 38.

It should now be clear that the slope control is set with its input angle $\theta$ by way of angle thumbwheel switches 56. Then, upon closing the load switch 58 the sine register 67 and the cosine register 69 are successively loaded with information regarding the sine and cosine functions of the input angle as obtained from the memory 60. Then, each time the turntable 41 completes a revolution, it hits the switch 73 on the index control 74 during the indextime of a scan causing the index control 74 to provide a number of clock pulses as preset by its dial 76. The index control 74 may be of the type as disclosed in U.S. Pat. No. 3,721,118. These preset clock pulses upon being proportioned through the sine BRM 71 and the cosine BRM 72 in accordance with the contents of the sine register 67 and the cosine register 69 operate to drive the stepping motors 13 and 30 and move the transducer 38 along a slope a predetermined distance as determined by the number of preset clock pulses supplied by the index control 74.

A more detailed description of the curvature control will next be presented in connection with FIGS. 8, 9 and 10 which are more detailed showings of the block functions in FIG. 6.

Specifically, the overall block diagram of the digital control system shown in FIG. 6 and the more detailed block diagram in FIG. 8 include additional functional blocks which enable the system to operate as a curvature control. In other words, the curvature control takes advantage of the fully digital programmable slope control as previously described. The curvature control, however, provides for advancing the transducer 38 along chords of ½° angles as defined along a circumferential path having any specified initial angle and a preset radius as compared to the slope control which provides for advancing the transducer along an inclined path having a fixed preset angle.

It should now be clearly understood that the curvature control provides for the transducer 38 to be incrementally moved along half degree chords of a circumference having a selected radius, as particularly shown in FIGS. 3, 4 and 5. Further, the curvature control provides for gimballing the transducer 38 about its gimbal point 27a a half degree each time it is indexed along a chord. The reason for this is that the beam of the transducer 38 must at all times be normal to the surface of the workpiece 40 being tested because the beam must be reflected back and sensed by the transducer 38 to determine if a flaw is present in the workpiece 40.

One of the problems which arises in the use of the radius control is that the unit pulses used to advance the transducer 38 along a linear path, as described for the slope control, must be modified in order for these unit pulses to be used to define the movement of the transducer 38 along chords of ½° angles at any specified radius. Such a chord definition is needed to determine when the transducer should be gimballed a half degree during the index time of a scan in order to maintain it normal to the surface being scanned.

First to be understood is that the chord of a 1 inch radius rotating ½° has a value of 8.73 pulses where each pulse corresponds to 0.001 of an inch. Thus the concept is to use the one inch radius as standard. However, it is not possible to provide 8.73 clock pulses. What is done is to pass 8 of them and then after 11 clock pulses, sufficient error is accumulated to warrant having another pulse. It is necessary, therefore, to provide the pulse unit modifier 80 to correct for the inability to show the chord of a ½° for a one inch radius in even units. Thus, as shown in FIG. 8, a binary 11 counter 90 is provided in the pulse unit modifier which counts preset clock pulses as provided by index control 74 (each such pulse is equal to 0.001 of an inch) and triggers a one-shot multivibrator 91 each 11th pulse which after a small delay of 5 microseconds introduces an additional pulse into a second one-shot multivibrator 92. The result of adding a pulse to the preset clock pulses provided by the index control 74, after every 11 pulses, in effect, results in modifying the unit value of each preset clock pulse to compensate for a cumulative error between a linear and radial axis. These modified unit clock pulses are then routed to the modulo $n$ counter 81 which functions as a radius adjuster. This modulo $n$ counter 81 is setup by the radius thumbwheel switches 82. It is a radius increment divider but in reality it is a multiplier since it deletes pulses in accordance with its modulo $n$ and determines the movement of the transducer 38 along a linear path, i.e., the length of a chord before the angle changes by ½ a degree. It should now be clear that when the radius in the thumbwheel switches 82 is put into the modulo $n$ counter 81, this latter waits until a number of modified pulses corresponding to the chord for that radius is counted before it supplies an output. Obviously, the larger the radius set up in the radius thumbwheel switches 82, the longer the length of the chord along the path of radial positioning of the transducer 38. When the modulo $n$ counter 81 emits a pulse LD (where $n$ is the radius of the path of the transducer gimbal point 27a), this pulse LD corresponds to a ½° angle for that radius. It increments the angle setup in the angle counter 57, accordingly. Simultaneously, it provides a pulse to the pulse multiplier 84 which provides 5 output pulses for each input pulse. That is, five pulses are provided to the gimbal stepping motor 31 for each pulse LD received. This is because each pulse corresponds to a 0.5° change in the angle counter 57, whereas the gimbal stepping motor 31 steps only 0.1° in response to each pulse. It should be noted that the angle counter 57 can be made to count either up or down which means curvature control can be performed by moving the transducer 38 in either direction along the circumferential path followed by its gimbal point 27a, i.e., moving from an initially set angle to an angle either more positive or more negative.

In addition to triggering the pulse multiplier 84, the output pulse LD of the modulo $n$ counter 81 triggers the register control 66 causing it to first request the sine function from the memory 60 for loading in the sine register 67, and then to subsequently request the cosine function from the memory 60 for loading in the cosine register 69. Actually this is preferably done each time the workpiece 40 revolves a single turn, that is, during the index time of a scan. Accordingly, it should now be clear that each time the workpiece 40 rotates on the turntable 41, as particularly shown in FIGS. 4 and 4a, the transducer 38 is repositioned along a chord of a ½° angle by the simultaneous movement of the X and Z stepping motors 13 and 30 caused by the clock pulses passing through the sine BRM 71 and the cosine BRM 72. Simultaneously, the pulse unit modifier 80 and the modulo $n$ counter 81 are actuated to measure the length of the chord such that when the proper length of the chord has been reached for a ½° angle at the specified radius, a pulse output from the modulo $n$ counter 81 causes the transducer 38 to be rotated about its gimbal point 27a one half degree such that its beam is directed inwardly to the center of the radius of the workpiece 40, and simultaneously, the sine register 67 and cosine register 69 are loaded with new information from the memory 60 to provide for indexing the transducer 38 along the new chord at the next index time of the scan.

Next to be described is the process whereby the curvature control of the present invention enables the nondestructive testing of workpieces having very small radii on the order of say 1 inch. This process is referred to as testing with a virtual scan. A typical setup for a virtual scan is shown in FIG. 4. The setup formula for such a scan is determined by the formula $r_2 = o_p + w.p. - r_1$ where $r_2$ is the radius set into the radius thumbwheel switches 82, $o_p$ is the pivot offset between the gimbal point 27a and the face 39 of the transducer 38, $w.p.$ is the water path or focal length of the ultrasonic beam of the transducer 38, and $r_1$ is the small radius of the concave surface on the workpiece 40 being scanned. It should be further noted that inasmuch as the ½° chord at radius $r_2$ is the programmed index increment $I_i$, the beam index increment is found by the formula $I_b = (r_2/r_1) I_i$ where $I_i$ is the index increment in inches, i.e., the index increment of the gimbal point 27a of transducer 38 along its circumferential path; and $I_b$ is the beam increment in inches, i.e., the incremental increment between successive scan paths on the surface of the workpiece being inspected.

It should now be clear that to perform a virtual scan, the transducer 38 is necessarily positioned a substantial distance away from the workpiece 40 as determined by the combined distances of the pivot offset, $o_p$, and the water path, $w.p.$, of the transducer. As previously explained, the water path is determined by the focal length of the beam which is focused into the surface of the workpiece 40 or just below the surface thereof.

It should now be evident that because of the physical problems of locating the transducer relative to a small radius concave surface of the workpiece to be scanned, it is necessary to perform a virtual scan. Thus in FIG. 4, a workpiece is shown with a curved surface 51 having a small radius $r_1$ on the order of 1 inch, for example. Since the transducer can not be physically positioned to have its gimbal point 27a located at the center 52 of the surface 51, the gimbal point 27a of the transducer 38 is positioned a distance away from the curved surface 51 equal to the pivot offset $o_p$ of the transducer plus the water path, $w.p.$ As a typical example, assuming the pivot offset $o_p$ is 4 inches and the water path, $w.p.$, is 3 inches, the gimbal point 27a of the transducer 38 is setup 6 inches from the center 52 of the curved surface 51 and 6 inches is dialed into the radius thumbwheel switch 82. It is really a 1 inch radius but 6 inches is dialed into the thumbwheel switches 82 because in order to perform the scan it is necessary to gimbal about the radial center 52 of the surface 51, and not along the surface 51 itself. By gimballing the beam about point 52, the beam is caused to sweep about the curved surface 51. Now since the surface 51 is to be inspected for 90°, the transducer 38 is initially directed down toward the vertical edge 59 of the workpiece and is controlled so that the beam pivots about point 52 such that the sound beam is at all times aligned with the radius.

It should now be further clear that to perform a virtual scan by use of the radius control, where the transducer 38 is indexed and gimballed along a circumferential path, the starting angle is preset into the control panel 49 along with the radius from the gimbal point 27a of the transducer to the radial center of the curved surface 51 on the workpiece to be inspected. Then the index limit which in this case is 90° is set up on the control panel 49.

Assume the workpiece 40 to be inspected is a typical turbine design as shown in FIG. 4, and it is desired to inspect the curved surface having a 1 inch radius $r_i$ shown. The transducer is initially manually positioned to the point shown, that is, so as to be directed down to the lip 59. The angle $\theta$ equal to 180 degrees is then set in the thumbwheel switches 56. The gimbal point 27a of the transducer is actually spaced a total of 7 inches from the curved surface 51 of the workpiece because of the pivot offset and the focal length of the transducer 38. However, the operator dials in 6 inches into the radius thumbwheel switches 82 in order to actually gimbal about the center point 52 of the curved surface 51 of the workpiece. The load switch 58 is then closed and the register control 66 requests from memory 60 the sine and cosine functions for 180° which are loaded into the sine register 67 and the cosine register 69. At the index time of the rotation of the turntable 41, the preset clock pulses, pcp, from the index control 74 are made available. These clock pulses upon passing through the sine BRM 71 and the cosine BRM 72 cause the transducer to move an appreciable amount of longitudinal distance in a straight line type of action or in reality the transducer moves along the chord of a 0.5° angle. Simultaneously the clock pulses from index control 74 pass through the pulse unit modifier 80 and are counted by the modulo $n$ counter. When an output pulse LD is provided from modulo $n$ counter 81 indicating that a chord of one half degree has been defined, the angle counter 57 is incremented by a half degree to 180.5°, the pulse multiplier 84 is initiated to provide 5 pulses to translator 85 to gimbal the transducer 38 one half degree about its gimbal point 27a, and the register control 66 is initiated to read out the sine and cosine functions of the new angle 180.5° out of the memory 60 into the sine and cosine registers 67 and 69. FIG. 4a illustrates, in a greatly exaggerated manner, the advancing of the transducer 38 and the gimballing thereof such that the transducer is aligned with a new radial line from the curved surface 51 when it is advanced a half degree as above described. It should now be clear that as the curvature control continues the transducer 38 progresses along the circumferential path and the workpiece curved surface 51 for the 90° limit desired. Thus, if this is a 90° sweep, 180 such chords will be performed.

Referring back to FIG. 3, assume that the transducer is provided with a 4 inch offset from the gimbal point 27a to the transducer face 39 and that the transducer requires a 5 inch focal path. This dictates that the gimbal pont 27a should be 9 inches away from the curved surface 45 of the workpiece. But more significantly, to perform the scan over the curved surface 45, the gimbal point 27a must be 10 inches away from the center point of the convex curved surface 45 which has a one inch radius. So 10 inches is dialed into the radius thumbwheel switches 82, and the transducer 38 is manually positioned 10 inches away to look down toward edge 70. Since the starting angle $\theta$ is 135 degrees, this angle is dialed into the thumbwheel switches 56 of control panel 49. Thus, two numbers are dialed in, the 10 inch radius and the 135° initial angle. Note that it is possible to keep track of the distance along the chords either by tracking the arc of the circumference or by tracking the distance along the chords. That is, both parameters are available. It should be noted that inasmuch as the system is operating along chords and not true exact arcs, there will be some few thousandths of error, the bigger the radius set in the thumbwheel switch 82, the larger the error. However, the error is relatively insignificant unless the system is operating with radii on the order of 100 inches. In other words, it can effectively be said that the path formed by these increments or chords is the circumference for all practical purposes. So it is possible to say that the index limit is going to be 45° or some linear distance equal to the combined lengths of the chords of ½° for a total arc at the specified radius.

The control panel 49 for the system is shown in FIG. 11. Thus to perform slope control the toggle switch 96 is set to be pointed toward its "vector" position. Assuming the workpiece 40 shown in FIG. 3 is to be tested, the angle $\theta$ equals 90 which corresponds to the angle that the surface 43 to be tested makes with the horizontal is then set up in the angle thumbwheel switches 56. The "jog" control is then used to properly initially position the transducer 38 with its axis normal to the surface 43 to be tested. Thus, by moving the toggle switch 97 to its "W.P." position, the transducer 38 can be controlled by toggle switch 98 to be incremented or decremented along its "W.P." axis (FIG. 3) such that the face 39 of the transducer 38 is spaced from the surface 43 to be tested by the focal length thereof. By moving the toggle switch 97 to its "NORM" position the transducer 38 can be controlled by toggle switch 98, which is normally in a neutral position, to be moved in either a forward or reverse direction along its normal path of travel so as to align the beam with the desired starting point, for example, the bottom edge 101 of the surface 43 of the workpiece to be inspected. The desired rate of the clock pulses to be supplied by the index control 74 is then set by rotating dial 100 which varies from 0 to 200 pulses per second. Now then by closing the load switch 58, a signal is supplied to activate register control 66 to cause the sine and the cosine functions of the input angle $\theta$ set up in the thumbwheel switches 56 to be read from memory 60 and loaded in the sine and cosine registers 67 and 69. Thereafter, each time the turntable 41 rotates, which is on the order of 10 to 20 rpm, it closes switch 73 on the index control 74 causing a proportional number of the preset clock pulses, depending on the sine and cosine functions read from the memory, to be routed through the sine BRM 71 and the cosine BRM 72 which respectively supply the X and Z clock pulses to reposition the transducer.

To perform curvature control on the curved portion 45 of the workpiece 40, the angle $\theta$ set up in the angle thumbwheel switches 56 of the control panel 49 is the starting angle only of the operation. In this case the input angle is 135°. The radius at which the gimbal point 27a of the transducer 38 is positioned relative to the curved surface 45 to be scanned is set up in the radius thumbwheel switches 82 of the control panel 49. In this case the radius is assumed to be 10 inches. The transducer 38 is then manually positioned by use of the jog toggle switches 97 and 98 along the "W.P." axis and then the "NORM" axis to its initial starting position. The load button 58 is then pressed and thereafter the curvature control provides for counting the modified unit pulses from the index control 74. Each time a chord of a half degree at the preset radius is defined, the angle counter 57 is advanced by a half degree, the gimbal stepping motor 31 is actuated to gimbal the transducer 38 by a half degree, and the sine and cosine functions of the new angle in the angle counter 59 are strobed from the memory 60 and loaded into the sine and cosine registers 67 and 69 which respectively operate to control the sine BRM 71 and the cosine BRM 72 to provide the clock pulses to move the transducer 38 along the next chord. It should be noted that the angle counter 57 is an up-down counter such that the transducer can be made to move in either a forward or reverse direction in one half degree increments. The toggle switch 94 on the control panel 49 determines which direction the movement will take place. The light emitting diode angle display 55 provides the operator with a visual indication of the angle at any instant of the curvature control operation. The operation of the slope control or the curvature control can be made to be continuous over a range as defined by the index limit. Thus, if it is desired, for example, to have the slope control continue for a specified distance as measured along the Z axis, the X axis, the Vector axis (hypotenuse) or for a given number of degrees (curvature control), the desired axis is selected by rotating switch dial 105. It should be noted that the setting of the range thumbwheel switches 107 is either in 0.001 of an inch or 0.1°, as appropriate for the axis selected by the switch. A light emitting diode index limit display 108 shows the position of the transducer along the selected axis at any instant during its operation.

An "on-off" limit switch 109 if "on" will operate to turn off the system when the reading on the display 108 matches the index limit as set up in the range thumbwheel switches 107. A light bulb 110 may be caused to be illuminated to indicate that the operation has been completed.

A program element 115 shown in FIG. 12 may be used in lieu of the control panel 49 shown in FIG. 11. Thus the program element 115 enables one step of a series of operations to be performed by the ultrasonic tester. The program element 115 includes the thumbwheel switches 56 for setting up the $\theta$ angle, the thumbwheel switches 82 for setting up the radius in curvature control, and the thumbwheel switches 107 for the sequence limit, i.e., the index limit for the step in the program represented by the program element 115. The mode of operation, i.e., whether slope control or curvature control, is selected by toggle switch 96. A toggle switch 116 below the sequence limit thumbwheel switches 107 selected whether the setting of these thumbwheel switches corresponds to units of 0.1° or 0.001 of an inch.

As shown in FIG. 13, a series of such program elements 115 can be set up to provide for operating the transducer of the ultrasonic tester to automatically perform the testing of a series of surfaces in succession, each of which may be either a straight surface at any angle, or a curved surface at any radius. In addition, a program element 115 may be used to automatically reposition the transducer to align it up for a succeeding testing of a surface. Thus referring to FIG. 3, a first program element 115a may be setup to control the transducer 38 by use of slope control to scan the vertical surface 43 for a specified range corresponding to its length in inches as set up in the sequence limit thumbwheel switches 107. A second program element 115b may be set up operating in curvature control to reposition the transducer so that it will be normal to the slope surface 44. The radius is set up in the radius thumbwheel switches 82 for this operation. The positioning continues for an angular span as set up in the sequence limit thumbwheel switches 107. Note that the latter operation is merely a positioning action, no scan recordings are made. This may be accomplished by merely disconnecting the scan recording elements. Another program element 115c may then be set up to control the transducer by use of the slope control to scan the surface 44 for a range as indicated by setting the length of the surface in the sequence limit thumbwheel switches 107. Another program element 115d may then be set up operating in curvature control to reposition the transducer to be normal to the beginning chord of the curved surface 45. This likewise is merely a positioning action. The next program element 115e can then provide for advancing the transducer by use of curvature control such as to inspect the curved surface 45. In this case the radius is set up in the radius thumbwheel switches 82 and the range of operation is set up in sequence limit thumbwheel switches 107. The program elements 115a – 115e can be sequenced by a counter (not shown) which is advanced each time the sequence limit of a program element has been reached and thereby enables the next program to be enabled.

It should now be clear that one of the most important advantages of the digital control system of the present invention is the ease with which the system can be programmed to perform its slope and curvature control operations. The simplicity of such programming is especially appreciated when it is understood that if a digital control system is able to perform radial operations at any radius and straight line operations at any angle, it is possible to scan any desired path on a rotating workpiece regardless of its shape.

While the digital control system shown and described herein is admirably adapted to fulfill the objects and advantages previously mentioned as desirable, it is to be understood that the invention is not limited to the specific features shown and described but that the means and configurations herein disclosed are susceptible of modification in form, proportions and arrangement of parts without departing from the principles involved or sacrificing any of its advantages and the invention, therefore, may be embodied in various forms within the scope of the appended claims.

What is claimed is:

1. A digital control system for indexing an operating unit along a sloped path including:
   a memory for storing sine and cosine functions,
   means for indicating an input angle corresponding to the slope of said path,
   a sine register and a cosine register,
   means responsive to the input angle for addressing said memory to load the sine and cosine functions of said input angle into said respective sine registers and cosine register,
   index control means for providing a number of clock pulses corresponding to the distance said operating unit is to be indexed along said sloped path,
   a sine proportion means and a cosine proportion means each passing portions of said clock pulses in accordance with the functions loaded in said respective sine register and cosine register, and
   a vertical axis stepping motor means and a horizontal axis stepping motor means simultaneously responsive to the portions of the clock pulses passed by said respective sine proportion means and cosine proportion means for indexing said operating unit along said sloped path.

2. The invention in accordance with claim 1 wherein said operating unit is an ultrasonic transducer.

3. The invention in accordance with claim 1 wherein said sine proportion means and cosine proportion means are binary rate multipliers.

4. The invention in accordance with claim 1 wherein said memory stores the sine and cosine functions of angles in the first quadrant, wherein the input angle may be in any of the four quadrants, and including means for correcting the input angle when in the second, third and fourth quadrants to a value for use in addressing the memory, whereby the sine and cosine functions of an input in any of the four quadrants may be strobed out of said memory.

5. The invention in accordance with claim 4 wherein said memory only stores sine functions of angles in the first quadrant in one half degree increments.

6. The invention in accordance with claim 4 including means for complementing the corrected angle for use in addressing the memory when the input angle is in the second and fourth quadrants.

7. The invention in accordance with claim 4 wherein said means for correcting the input angle further operates to provide the sign to be attached to said portions of the clock pulses passed by the sine proportion and cosine proportion means.

8. The invention in accordance with claim 1 including:

an index limiter for providing an indication of the range of the indexing of said operating unit along said sloped path, and means operating to terminate the indexing of said operating unit when the distance moved by said operating unit along said sloped path matches the indication of the range in said index limiter.

9. A digital control system for indexing an operating unit along a curved path which is concentric with a curved surface of a workpiece to be scanned by said operating unit, said system including:

counter means for providing an indication of the angle of the slope of a chord of a fixed angular increment along said curved path, index control means for providing clock pulses, each pulse corresponding to a fixed linear increment, chord measuring means responsive to said clock pulses to provide an output when a chord of said fixed angular increment along said curved path has been measured, said counter means responsive to said output to change the indication of the angle therein by said fixed angular increment, a gimbal motor stepping means responsive to said output to gimbal the operating unit about said curved path by said fixed angular increment, a memory for storing sine and cosine functions of angles in said angular increments, means responsive to the indication of the angle in said counter means for addressing said memory, a sine register and a cosine register, register control means responsive to said output to strobe said memory in accordance with the means provided for addressing said memory to load the sine and cosine functions of the angle in said counter means in said respective sine register and cosine register, a sine proportion means and a cosine proportion means associated with said respective sine register and cosine register, said sine proportion means and cosine proportion means being responsive to the clock pulses from said index control means to pass portions thereof in accordance with the functions loaded in said respective sine register and cosine register, and a vertical axis stepping motor means and a horizontal axis stepping motor means simultaneously responsive to the portions of the clock pulses passed by said sine proportion means and cosine proportion means for indexing said operating unit along a succeeding chord of said fixed angular increment along said curved path.

10. The invention in accordance with claim 9 wherein said operating unit is an ultrasonic transducer.

11. The invention in accordance with claim 9 wherein said sine proportion means and cosine proportion means are binary rate multipliers.

12. The invention in accordance with claim 9 wherein said chord measuring means includes:

radius indicating means for indicating the distance of the curved path from the center of curvature of the curved surface of the workpiece being scanned, a pulse unit modifier for modifying the increment represented by the clock pulses so that a fixed number of pulses can be counted to define a chord of said fixed angular increment along a curved path having a radius of one inch, and a modulo $n$ counter for counting the modified unit pulses in accordance with the setting of said radius indicating means and providing an output when a chord of said fixed angular increment along said curved path has been measured.

13. The invention in accordance with claim 9 wherein said fixed angular increment is a half degree angle.

14. A method of performing the virtual scan of a curved surface with the focussed beam of an ultrasonic transducer having a gimbal point, said method comprising:

positioning the transducer with its axis aligned along a radius of said curved surface and its face spaced from the curved surface by a distance substantially equal to the focal length of its beam, moving the gimbal point of said transducer along a chord of a fixed angular increment defined along a curved path having a radius equal to the pivot offset of the face of said transducer plus the focal length of said transducer minus the radius of said curved surface, and gimballing said transducer said fixed angular increment about its gimbal point such that the axis of said transducer is again aligned with a radius of said curved surface.

15. The method in accordance with claim 14 wherein the combined distance of the face of the transducer from its gimbal point and the focal length of the beam of said transducer along the axis thereof is greater that the radius of said curved surface.

16. The method in accordance with claim 14 wherein the moving of the gimbal point of the transducer along a chord of a fixed angular increment defined along said curved path includes the steps of defining the angle of the slope of said chord, providing the sine and cosine functions of the angle of the slope of said chord, providing a source of index clock pulses, passing portions of said index clock pulses in accordance with said sine and cosine functions to provide vertical and horizontal clock pulses, and moving the gimbal point of said transducer along said chord by simultaneously moving it along a vertical axis and a horizontal axis in accordance with said vertical and horizontal clock pulses.

17. A method of scanning a curved surface with the focussed beam of an ultrasonic transducer having its face offset from a gimbal point thereon, said method comprising:

positioning the transducer with its axis aligned along a radius of said curved surface and its face spaced from the curved surface by a distance substantially equal to the focal length of its beam, moving the gimbal point of said transducer along a chord of a fixed angular increment defined along a curved path having a radius equal to the pivot offset of the face of said transducer plus the focal length of said transducer, and gimballing the transducer about its gimbal point said fixed angular increment such that the axis of said transducer is again aligned with a radius of said curved surface.

18. A method of scanning a curved surface with the focussed beam of an ultrasonic transducer having its face offset from a gimbal point thereon, said method comprising:

positioning the transducer with its axis aligned along a radius of said curved surface and its face spaced from the curved surface be a distance substantially equal to the focal length of its beam, moving the gimbal point of said transducer along a chord of a fixed angular increment defined along a curved path having a radius equal to the pivot offset of the face of said transducer plus the focal length of said transducer and the radius of said curved surface, and gimballing the transducer about its gimbal point said fixed angular increment such that the axis of said transducer is again aligned with a radius of said curved surface.

19. A digital control system for incrementally advancing an operating unit along successive chords of a circumferential path comprising:

a vertical axis and a horizontal axis stepping motor means, a memory storing sine and cosine functions, an angle counter settable to an angle corresponding to the slope of a chord of said circumferential path along which said operating unit is to be moved, a source of pulses each corresponding to a fixed linear increment, a sine and cosine proportion means, control means operable to address said memory with the angle in said angle counter and to set said sine and cosine proportion means to pass pulses from said source in accordance with the sine and cosine functions of said angle, said vertical axis and horizontal axis is stepping motor means being responsive to the portions of the pulses passed by said respective sine and cosine proportion means for incrementally advancing said operating unit along said chord, a gimbal axis stepping motor means, and a chord measuring means responsive to pulses from said source and operable when the length of a chord is measured to provide an output to said angle counter to change it by a fixed angular increment corresponding to the chord and to said gimbal axis stepping motor means to gimbal said operating unit by said fixed angular increment.

20. The invention in accordance with claim 19 wherein said chord measuring means includes a counter means having a counting cycle corresponding to the length of a chord of a unit radius, and including radius setting means for modifying said counter means to provide an output defining the length of said chord at any selected radius.

* * * * *